(12) United States Patent
Zouridakis et al.

(10) Patent No.: US 8,213,695 B2
(45) Date of Patent: Jul. 3, 2012

(54) DEVICE AND SOFTWARE FOR SCREENING THE SKIN

(75) Inventors: George Zouridakis, Houston, TX (US); Xiaojing Yuan, Pearland, TX (US); Ji Chen, Pearland, TX (US); Eric Stotzer, Houston, TX (US); Yanmin Wu, Sugarland, TX (US)

(73) Assignees: University of Houston, Houston, TX (US); Texas Instruments Incorporated, Dallas, TX (US)

( * ) Notice: Subject to any disclaimer, the term of this patent is extended or adjusted under 35 U.S.C. 154(b) by 1122 days.

(21) Appl. No.: 12/075,026

(22) Filed: Mar. 7, 2008

(65) Prior Publication Data

US 2008/0226151 A1 Sep. 18, 2008

Related U.S. Application Data

(60) Provisional application No. 60/905,405, filed on Mar. 7, 2007.

(51) Int. Cl.
*G06K 9/22* (2006.01)
*G06K 9/34* (2006.01)
*A61B 5/103* (2006.01)

(52) U.S. Cl. ......... 382/128; 382/173; 382/224; 382/313

(58) Field of Classification Search ........... 382/129–133
See application file for complete search history.

(56) References Cited

U.S. PATENT DOCUMENTS

| 6,417,797 | B1 * | 7/2002 | Cousins et al. | 342/179 |
| 6,473,831 | B1 * | 10/2002 | Schade | 711/115 |
| 7,006,223 | B2 * | 2/2006 | Mullani | 356/369 |
| 7,400,767 | B2 * | 7/2008 | Slabaugh et al. | 382/173 |
| 7,629,769 | B2 * | 12/2009 | Gangstoe et al. | 320/134 |
| 2005/0065418 | A1 * | 3/2005 | Ginor | 600/345 |
| 2006/0055793 | A1 * | 3/2006 | Adler et al. | 348/211.99 |
| 2006/0129848 | A1 * | 6/2006 | Paksoy et al. | 713/193 |
| 2006/0269111 | A1 * | 11/2006 | Stoecker et al. | 382/128 |
| 2009/0016650 | A1 * | 1/2009 | Bell et al. | 382/313 |

* cited by examiner

*Primary Examiner* — Jack Berman
*Assistant Examiner* — David E Smith
(74) *Attorney, Agent, or Firm* — Benjamin Aaron Adler

(57) ABSTRACT

The present invention provides devices for screening the skin of an individual in real time using a region-fusion based segmentation with narrow band graph partitioning algorithm to analyze and classify a region of interest of the skin as benign or malignant. Also, provided is a method for screening the skin of an individual using the devices described herein. In addition the present invention provides a digital processor-implemented system for classifying a region of interest on the skin and a processor readable medium having processor-executable instructions to perform skin cancer detection.

25 Claims, 8 Drawing Sheets

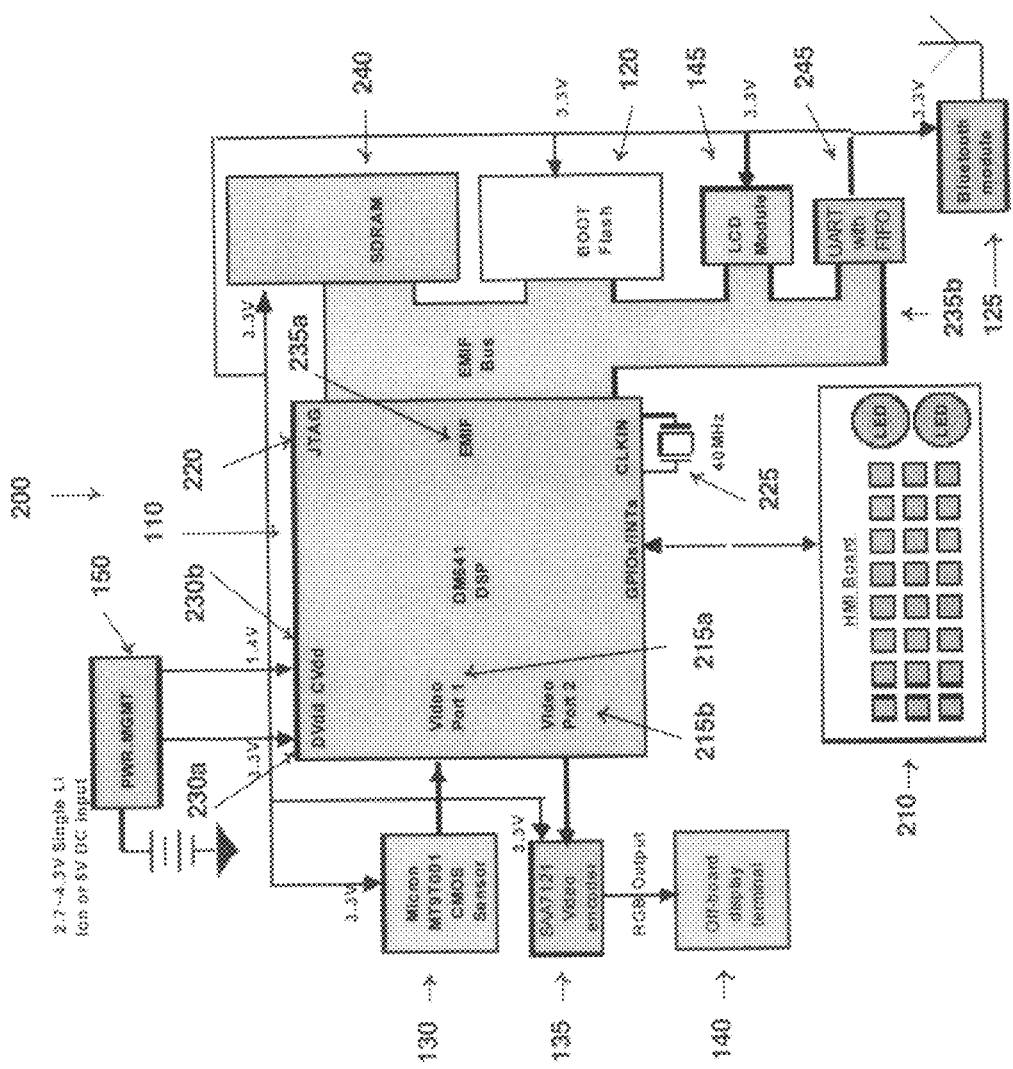

7.9%     4.71%     6.89%     36.199%

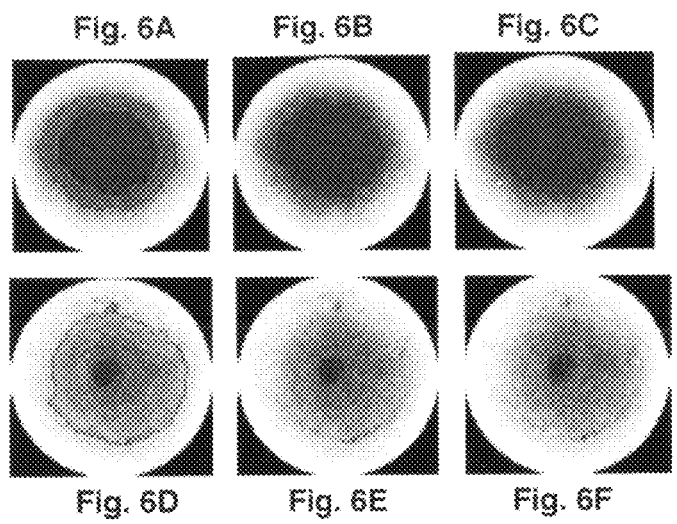
Fig. 6A  Fig. 6B  Fig. 6C
Fig. 6D  Fig. 6E  Fig. 6F
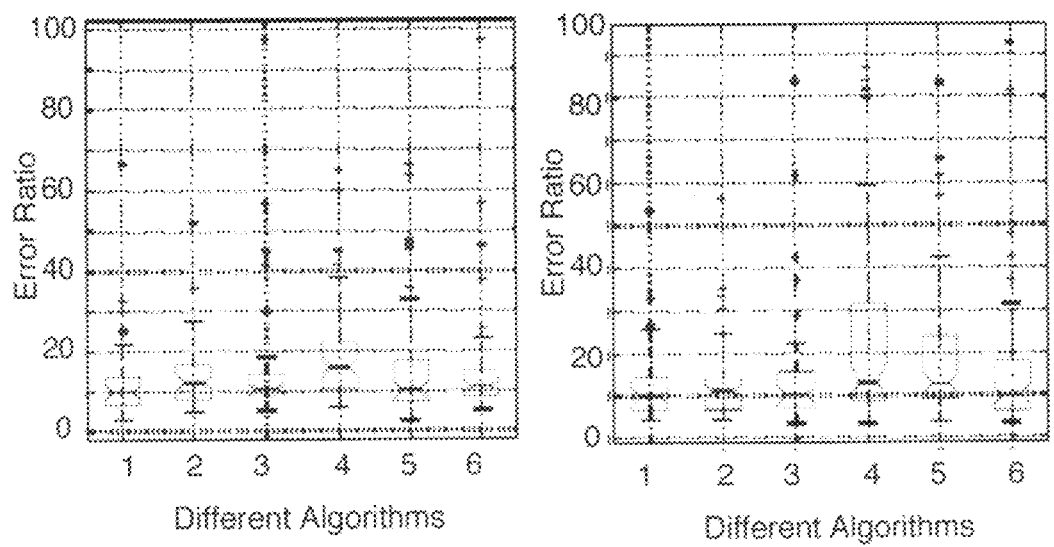
Fig. 7A  Fig. 7B

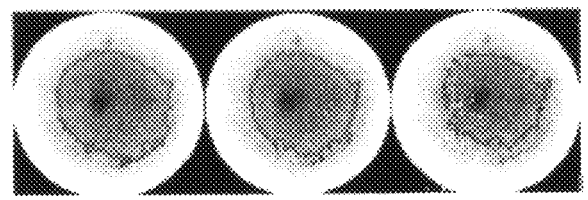
Fig. 8A    Fig.8B    Fig. 8C
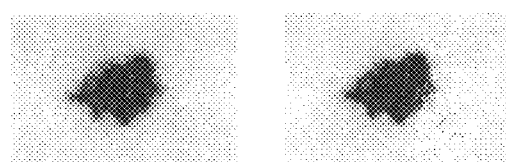
Fig. 9A    Fig. 9B
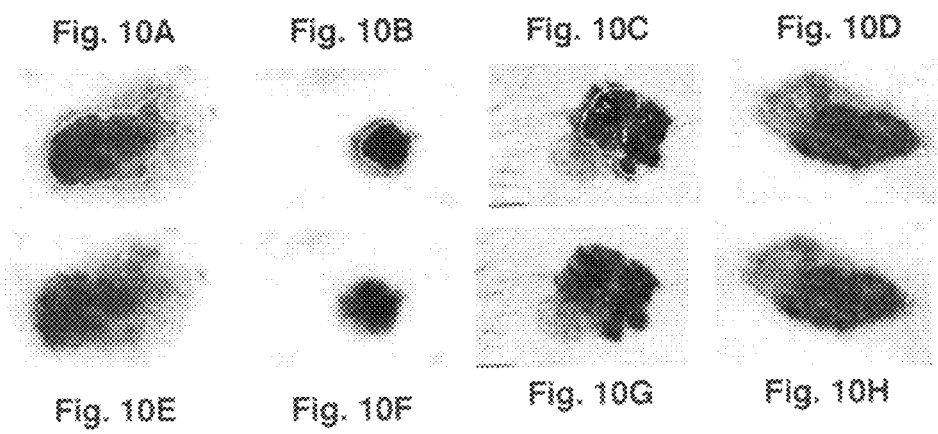
Fig. 10A    Fig. 10B    Fig. 10C    Fig. 10D
Fig. 10E    Fig. 10F    Fig. 10G    Fig. 10H

DEVICE AND SOFTWARE FOR SCREENING THE SKIN

CROSS-REFERENCE TO RELATED APPLICATIONS

This nonprovisional application claims benefit of priority of provisional U.S. Ser. No. 60/905,405, filed Mar. 7, 2007, now abandoned.

FEDERAL FUNDING LEGEND

This invention was produced in part using funds obtained through grant 521527 from the National Science Foundation. Consequently, the federal government has certain rights in this invention.

BACKGROUND OF THE INVENTION

1. Field of the Invention

This invention relates to the fields of biomedical screening devices and dermoscopy. Specifically, the present invention provides a handheld medical device and software useful for skin cancer screening in real time.

2. Description of the Related Art

Skin cancer is the most common form of cancer, representing about half the number of all cancer types. The most deadly form of skin cancer is melanoma for which incidences increase by 3% annually. Frequent screening of suspicious skin pigmentations and other lesions is of paramount importance since at an early stage skin cancer has a high cure rate and, in most cases, requires a simple treatment.

The American Cancer Society predicts that one in six individuals will develop skin cancer and one in nine will develop melanoma during their lifetime. The risk of melanoma is much higher in patients with dysplastic or clinically-abnormal pigmented nevi. A nevus, or mole, is a common skin growth composed of special pigment-producing cells called melanocytes, which determine the color of the hair and skin. Dysplastic nevi, occasionally referred as early melanomas, are skin lesions that carry high risk for melanoma.

Early detection of melanoma in patients with dysplastic nevi is life saving. If detected at an early stage, skin cancer has one of the highest cure rates, and in most cases, the treatment is quite simple and involves excision of the lesion. Moreover, at an early stage, skin cancers are very economical to treat, while at a later stage, cancerous lesions usually result in near fatal consequences and have extremely high costs associated with treatment.

In the case of malignancy, early changes in the nevus usually consist of an irregular pigmentation pattern, before it becomes lethal. Studies show that visual detection by a dermatologist has the average diagnostic accuracy of only 58 percent and about 30 percent for nonexperts, i.e., dermatologists who do not specialize in early melanoma detection. It is also known that diagnostic accuracy can be improved 80-93% by using imaging techniques like epiluminescence microscopy, to better visualize the pigmentation pattern, and by combining it with a clinically accepted quantitative scoring methods used by dermatologists for classification of lesions, such as the well-known A (asymmetry), B (border), C (color), and D (differentiation) rule and Menzies method, which is based on number of colors, symmetry of pattern, and the positive features of the lesion.

Existing imaging modalities rely mainly on pigmentation features of a lesion, such as shape, color, and texture. However, recent studies have demonstrated a correlation between increased blood flow and the development of new blood vessels by a malignant tumor (angiogenesis) to meet the high metabolic rate of a growing tumor.

Existing devices used to observe skin surface can only acquire pictures in one modality at a time, and the acquired pictures can not be readily processed. Though such devices find interesting uses, they present great limitations to users since the acquired images must be transferred to a personal computer for further analysis. Existing software only performs limited image analysis and fails to provide physicians with an unambiguous diagnosis.

Thus, there is a recognized need in the art for an integrated solution that combines image acquisition and automated image analysis in medical devices for skin cancer screening. More, specifically the prior art is deficient in portable handheld devices and software for skin cancer screening in real time. The present invention fulfills this long-standing need and desire in the art.

SUMMARY OF THE INVENTION

The present invention is directed to a device for screening the skin of an individual in real time. The device comprises means for programming of the device, means for controlling interaction with a user of the device, means for acquiring and displaying an image of a region of interest on the skin of an individual, means for analyzing and classifying the acquired image, means for controlling one or both of an exchange of data with a personal computer or a receipt of software from a personal computer. The present invention is directed to a related device further comprising means for powering the device. The present invention is directed to another related device further comprising means for housing the device that is both portable and hand-holdable.

The present invention also is directed to another device for screening the skin of an individual in real time. The device comprises a programmable digital signal microprocessor with a memory storing processor executable instructions digitally linked to other device components. The other components are a boot flash for parallel flash memory digitally connected to the microprocessor, an input device, a sensor having a combination of one or more light sources and one or more imaging sensors, a digital to analog signal video encoder connected to an off-board display terminal, an on-board display terminal, a wireless device configured to wirelessly communicate between the programmable digital signal microprocessor and a personal computer, including a parallel for a Universal Asynchronous Receiver/Transmitter, and a power management unit. The device also comprises a housing the device that is portable and hand-holdable.

The present invention is directed further to a method for screening the skin of an individual in real time. The method comprises holding the portable handheld device described herein over a region of interest containing a skin lesion on the individual, acquiring one or more images of the skin lesion in one or more modalities, displaying the acquired image, pre-processing the acquired image(s) using a region-fusion based segmentation with narrow band graph partitioning algorithm, classifying the region of interest on the skin as benign or malignant and displaying the classification results. The present invention is directed to a related method further comprising wirelessly communicating the classification results to a personal computer.

The present invention is directed further still to a digital processor-implemented system for classifying a region of interest on the skin of an individual. The system comprises a module for pre-processing and image segmentation of the region of interest, a module for image classification of a skin lesion found within the region of interest as a benign or malignant lesion as determined by one or more of a size difference, shape irregularity or texture formation each of which comprises a partial classification, a module for decision voting in terms of confidence based weighted averaging of the partial classifications, and a module for image reconstruction for three-dimensional imaging of the region of interest. The present invention is directed to a related system further comprising a module for wireless communication between the processor and a personal computer.

The present invention is directed further still to a processor readable medium having processor-executable instructions to perform a method for detecting skin cancers on an individual in real time. The method comprises the steps of acquiring one or more images of a region of interest on the skin in one or more modalities, preprocessing the acquired image(s) comprising extracting the lesion from the background of the image and determining a lesion border using a region-fusion based segmentation with narrow band graph partitioning algorithm, classifying the skin lesion as benign or malignant by a confidence based weighted averaging of a combination of partial classifications based on one or more features of the skin lesion, and displaying the classification results.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and, therefore, are not to be considered limiting in their scope.

FIGS. 2A-2B illustrate assembly of the generic system described in FIG. 1 showing prototype components (FIG. 2A) and depict the printed circuit board layout of the prototype components (FIG. 2B).

FIGS. 6A-6F show results of the segmentation of two TLM images. The TLM images show segmentation with Chan-Vese's method (FIGS. 6A, 6D), the region fusion of Chan-Vese's method (FIGS. 6B, 6E), and NBGP (FIGS. 6C, 6F).

FIGS. 7A-7B depict the error ratio of six segmentation methods on XLM images (FIG. 7A) and on TLM images (FIG. 7B). The x-axis identifies the methods as 1: NBGP, 2: Chan-Vese, 3: Scoring system, 4: PCT method, 5: Sigmoid-based PCT method, and 6: Fuzzy C-Mean.

FIGS. 8A-8C illustrate incorrect lesion segmentation for Sigmoid (FIG. 8A), PCT+Sigmoid (FIG. 8B), and Fuzzy C-mean (FIG. 8C) methods.

FIGS. 9A-9B depict segmentation results from the Chan-Vese model only (FIG. 9A) and the NBGP algorithm (FIG. 9B).

FIGS. 10A-10H depict segmentation results of asymmetric lesions. FIGS. 10A-10D show results from Chan-Vese's method. FIGS. 10E-10F show results from the NBPG method. For FIGS. 10C and 10G, a DullRazor method is used for hair removal.

In FIG. 11A the labels on the x-axis are: 1: NBGP, 2: Chan-Vese, and 3-5, three dermatologists. In FIG. 11B the labels on the x-axis are: 1-3: NBGP vs. manual results and 4-6: inter-dermatologists' variation.

DETAILED DESCRIPTION OF THE INVENTION

Figure 1:
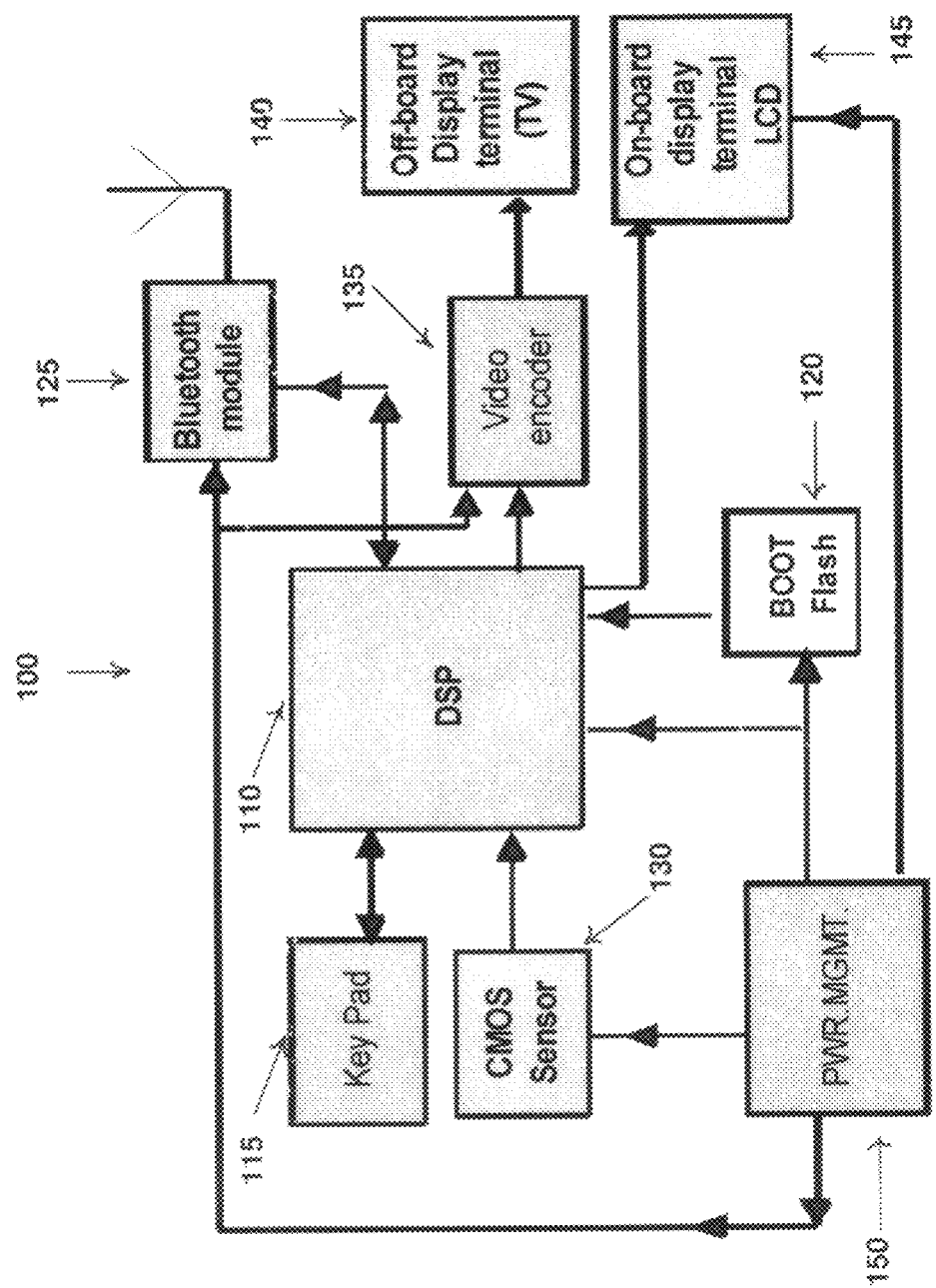
FIG. 1 is a generic system diagram describing the hardware of the portable battery-powered handheld medical device

As used herein, the term "a" or "an", when used in conjunction with the term "comprising" in the claims and/or the specification, may refer to "one," but it is also consistent with the meaning of "one or more," "at least one," and "one or more than one." some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

In one embodiment of the present invention there is provided a device for screening the skin of an individual in real time, comprising means for programming the device; means for controlling interaction with a user of the device; means for acquiring and displaying an image of a region of interest on the skin of an individual; means for analyzing and classifying the image; and means for controlling one or both of an exchange of data with a personal computer or a receipt of software from a personal computer.

Further to this embodiment the device comprises means for powering the device. Particularly, the means for powering the device may be a power management unit comprising a power management unit having a battery, a battery charger, a supervisor and voltage regulators. In another further embodiment the device further comprises means for housing the device that is both portable and hand-holdable.

In this embodiment the means for programming the device may comprise a programmable digital signal microprocessor with a memory storing processor executable instructions and a boot flash for parallel flash memory. Also, the means for controlling interaction with a user of the device may comprise a human machine interface board, including a keypad and one or more display terminals and a user interface. The display terminals may be one or both of an on-board display terminal or an off-board display terminal.

In addition in this embodiment the means for acquiring and displaying an image of the skin lesion may comprise a sensor having a combination of one or more light sources and one or more imaging sensors for image acquisition, a video encoder to convert the acquired digital image as an analog off board image and an on board visual display. Furthermore, the means for controlling one or both of an exchange of data with or receipt of software from a personal computer may comprise a device configured to wirelessly communicate between a programmable digital signal microprocessor comprising the handheld screening device and a personal computer, including a parallel for a Universal Asynchronous Receiver/Transmitter.

In another embodiment of the present invention there is provided a related device for screening the skin of an individual in real time, comprising a programmable digital signal microprocessor with a memory storing processor executable instructions digitally linked to: a boot flash for parallel flash memory digitally connected to the microprocessor; an input device; a sensor having a combination of one or more light sources and one or more imaging sensors; a digital to analog signal video encoder connected to an off-board display terminal; an on-board display terminal; a wireless device configured to wirelessly communicate between the programmable digital signal microprocessor and a personal computer, including a parallel for a Universal Asynchronous Receiver/Transmitter; and a power management unit; and a housing the device that is portable and hand-holdable.

In this related embodiment the input device may be a keypad or a touch screen. Also, the light source(s) may emit visible or invisible light arranged in different spatial configurations and the imaging sensor(s) may be an optical camera, an infrared camera, a thermal camera, a three dimensional stereo camera or a digital light processing sensor. In addition the power management unit may comprise a battery, a battery charger, supervisor, and two voltage regulators.

In yet another embodiment the present invention provides a method for screening the skin of an individual in real time, comprising acquiring one or more images of a region of interest on the skin in one or more modalities with the device described supra; displaying the acquired image; preprocessing the acquired image(s) using a region-fusion based segmentation with narrow band graph partitioning algorithm; classifying the region of interest on the skin as benign or malignant; and displaying the classification results. Further to this embodiment the method comprises wirelessly communicating the classification results to a personal computer.

In both embodiments the imaging modality is XLM or TLM. Also, preprocessing may comprise extracting the lesion from the background of the image and determining a lesion border. In addition classifying the lesion may comprise confidence based weighted averaging of a combination of partial classifications based on one or more features of the lesion. Examples of classifiable features are a size difference, shape irregularity or texture formation. Furthermore, displaying the classification may comprise color coding the results.

In yet another embodiment there is provided a digital processor-implemented system for classifying a skin lesion, comprising a module for pre-processing and image segmentation of the region of interest; a module for image classification of a lesion found within the region of interest as a benign or malignant lesion as determined by one or more of a size difference, shape irregularity or texture formation each of which comprises a partial classification; a module for decision voting in terms of confidence based weight averaging of the partial classifications; and a module for image reconstruction for three-dimensional imaging of the region of interest. Further to this embodiment the system comprises a module for wireless communication between the processor and a personal computer.

In yet another embodiment there is provided a processor readable medium having processor-executable instructions to perform a method for detecting skin cancers on an individual in real time, said method comprising the steps of acquiring one or more images of a region of interest on the skin in one or more modalities; preprocessing the acquired image(s) comprising extracting a lesion from the background of the image and determining a lesion border using a region-fusion based segmentation with narrow band graph partitioning algorithm; classifying the lesion as probably not malignant, possibly malignant or probably malignant by a confidence based weighted averaging of a combination of partial classifications based on one or more features of the lesion; and displaying the classification results.

In this embodiment the imaging modalities may be XLM or TLM. Also, the features of the lesion may include a size difference, shape irregularity or texture formation. In addition displaying the classification may comprise color coding the results.

Provided herein are devices, systems and methods for detecting skin cancer, including digital processor-implemented systems and a processor readable medium. The present invention is a portable battery-powered handheld medical and software for early detection of skin cancer. Such device finds relevant uses among the medical community. The device is the size of a cell phone that physicians can use to assist with skin cancer screening. The handheld medical device captures multi-spectral, multi-modal images of a skin lesion, while the software processes the acquired images in real-time, and then executes computational decision algorithms to determine the probability that a skin lesion is cancerous.

The present invention is particularly relevant to general practitioners and specialized dermatologists for early skin cancer diagnosis. As a result, it increases the probability of a patient's complete cure, and overall helps decrease the morbidity and mortality rates of skin cancer. However, it is contemplated that the handheld skin cancer detecting device provided herein could lead to general-purpose devices that are scalable and adaptable to other areas of medicine, such as vein-disease detection and wound healing.

Also, the use of self-contained, smart, programmable, pocketsize devices has the potential of revolutionizing health care delivery at the primary care level. Such devices can provide an unbiased and consistent analysis of images and thus their deployment on a large scale at the level of primary care can assist physicians make accurate, reliable, and fast decisions that are beneficial to large numbers of patients. In addition, network-connected smart devices, such as the one proposed, can assist general practitioners in remote areas to improve the quality of care by connecting to, and comparing patient data against, large databases and/or centralized points of service where specialists are on call.

One of the objects of the present invention therefore relates to a convenient handheld device used for the imaging and detection of early forms of skin cancers, using a desired image modality or a combination of desired modalities. The device is a self-contained handheld imaging device about the size of a cell phone for automated detection of melanoma. In order to meet the small size and low power requirements of a portable device, an embedded microprocessor is used. The microprocessor should has a general purpose and fully programmable architecture with sufficient computational power to implement all existing algorithms of the automated system for screening melanoma, as well as to accommodate additions of new algorithms.

This real time system can capture and process 1280×720 resolution images at the rate of 30 frames/second. It has also the capability of sending images to a remote server through a Bluetooth module for data storage. It is designed to be a development platform that allows researchers to use the full speed at 5760 million instructions per second (MIPS) of the processor for experimentation and development of sophisticated image processing algorithms for skin cancer detection and also as a reference design board, that can speed up the commercialization of a Bluetooth-enabled portable skin cancer detector.

A low noise CMOS image sensor converts the incoming pictures into digital signals. Once the data are converted to the digital domain, the DSP processes the digital stream using the various algorithms for detecting malignant legions. Then a high-performance low-noise video encoder (the digital-to-analog converter) is used to convert the processed digital data back to an analog signal. The analog signal drives a display terminal, such as an LCD, for real-time display. All processed images can be sent out to a remote server through the Bluetooth module for further processing and storage. A keypad and LCD provide the human machine interface (HMI) function. The power management module (PWR.MGMT.) includes various switching regulators to meet the voltage requirements of the different blocks in the system.

This system consists of several key components: a 3M pixel CMOS sensor streams high-resolution images into DSP. The high-resolution images require tremendous processing power and large data and program memory. The limited-size on-chip memory of the DSP requires that external SDRAMs be added to the system. A video encoder converts the digital signal back to analog for real-time image display. A parallel boot flash is used for program storage. A UART transceiver is added into the system for interfacing with the Bluetooth module. This prototype system is designed with an HMI board and includes buttons and LEDs that enable the user to control and monitor the system function. An 8-bit latch extends control I/Os, and power regulators generate 1.4V-core voltage and 3.3V I/O voltage for the DSP as well as other chips. The DSP has several power-down modes to minimize power consumption when idle. The 1.4 core voltage of the DSP can be reduced to 1.2 V with optimized software (reduced MIPS consumption) and the CPU clock can be slowed down for further power saving.

FIG. 1 is a generic system diagram that shows how these elements and components are interconnected (memory and parallel to UART not shown). This system diagram is not limited to the components and units depicted, but has been designed to accommodate other elements depending on the imaging and software needs.

The system/device 100 comprises a programmable digital signal (DSP) microprocessor 110 with one or more cores and a memory (not shown) (SDRAM MT48LC4M32B2, Micron) for external memory used by the programmable digital signal processor and a key pad 115 as input device, including but not limited to a touch screen and keypads. The DSP may be a video/imaging fixed-point digital signal processor (DM641, Texas Instruments). A boot flash architecture 120 (AM29LV033C, AMD) for parallel flash memory is linked to the programmable digital signal processor. The system includes a human machine interface (HMI) for user compatibility.

The programmable DSP is linked to a module 125 enabling short range wireless connectivity, e.g., Bluetooth® (EYMF2CAMM, Taiko Yuden), that converts Universal Asynchronous Receiver/Transmitter (UART) data from the programmable digital signal processor to a wireless signal receivable by a personal computer (not shown). A parallel to a UART (TL16C752B, Texas Instruments) with first-in first-out (FIFO) (not shown) provides an interface between the programmable digital signal processor and the Bluetooth® module.

A sensor 130, e.g., a CMOS sensor (MT9T001, Micron), comprises a combination of one or more light sources, including but not limited to emitting visible or invisible light arranged in different spatial configurations and one or more imaging sensors that is sensitive to light of different frequencies, including but not limited to optical cameras, infrared cameras, thermal cameras, three dimensional stereo cameras, and digital light processing (DLP) sensors input images into the programmable digital signal processor.

The programmable digital signal processor 110 sends imaging signals to a video encoder 135 (SAA7121, Philips) comprising a digital/analog converter which converts the digital imaging signal to an analog signal which is transmitted to an off-board display terminal 140, e.g., a TV, and decoded via an AV decoder (not shown) (TMS320DM641, Texas instruments) for off-board display. The digital imaging signal also may be transmitted to an on-board display terminal 145, e.g., a liquid crystal display (LCD) (LQ022B8UD04, Sharp). A power management unit 150 may include a battery charger, supervisor, and two voltage regulators to supply the necessary voltages to all components. For example, the power management unit may comprise a power regulator (TPS3306, Texas Instruments) and a power supervisor (TPS54310, Texas Instruments).

Serial ports are used to display the captured images onto the external monitor directly. MATLAB based algorithms are re-designed and ported to the fixed point DSP-based prototype. A user-friendly HMI as well as image storage and transmission are also developed. The software utilizes DSP BIOS to create a multi-thread real time system. HMI, video capture/display, Bluetooth driver as well as segmentation algorithms, are implemented. The prototype can process previously acquired XLM and TLM images as well as the real-time captured images. In addition, it can transmit images to a remote PC through Bluetooth for storage or further processing. The developed systems can segment and classify images correctly as malignant or benign based on normalized the area percent increase between XLM and TLM images.

With continued reference to FIG. 1, FIG. 2A is a schematic showing how the system 100 is built, including necessary voltages to run the system/device. As is standard, the programmable video/imaging fixed-point digital signal processor 110 comprises general purpose inputs/outputs ports and interfaces, for example, to connect to the HMI board 210, a video port 215a connecting to the sensor 130, a video port 215b to connect to the video encoder 135, a joint test action group (JTAG) adapter 220, an analog input pin 225 with a CLKIN frequency of about 40 MHz, power regulators DVdd 230a to regulate I/O supply voltage and CVdd 230b to regulate core supply voltage each of which is connected to the power management unit (PWR MGMT) 150, and an external memory interface (EMIF) 235a and EMIF bus 235b. The video encoder 135 comprises an RGB output 240 connecting to the off-board display terminal 140.

The EMIF bus 235b provides for interfacing with the memory 240, the boot flash 120, the LCD module 145, and the UART with FIFO 245. The UART data from the programmable digital signal processor is converted to a wireless signal via a module 125, e.g., a Bluetooth® module, subsequently received by a personal computer (not shown).

Figure 2B:
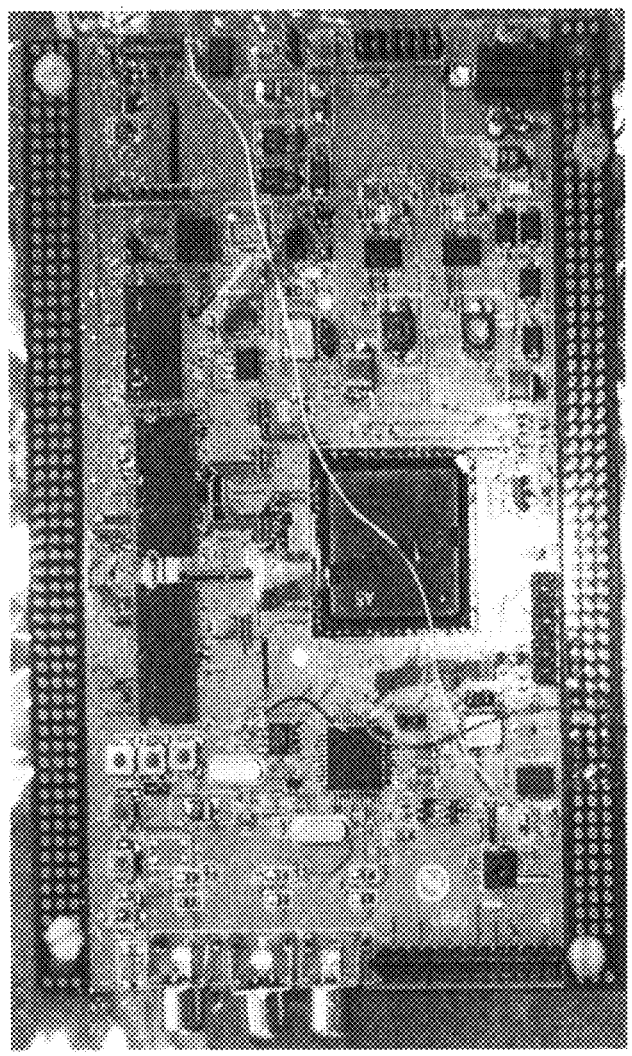

FIG. 2B is a printed circuit board 250 layout of the system diagram depicted in FIG. 2A. This printed circuit board represents the hardware of the portable battery-powered handheld medical device.

Also provided herein are processor-implemented software modules and algorithms that allow classification of lesions to be performed on the handheld device itself. The present invention is self-contained and readily upgradeable with the latest imaging and processing technologies. The programmable microprocessor runs the software which 1) controls image acquisition, image analysis, and lesion classification, 2) controls the interaction with the user via the interactive input interface, such as, but not limited to a touch screen, key pad, and voice recognition and 3) controls the data exchange with and receiving software from a personal computer wirelessly via a device such as Bluetooth®.

The decision support software is expandable to satisfy imaging needs. The software can acquire images using many different types of light conditions, including, but not limited to regular light, infrared, ultraviolet, blue light, as well as many different types of modalities, such as, but not limited to epiluminescence microscopy, cross-polarization, side-transillumination, and three-dimensional mode. The software processes the acquired images performing tasks such as, but not limited to image segmentation, multiple feature extraction from the lesion, such as, but not limited to area calculation, pigmentation, and texture analysis. Also, screening results may be presented using a color coded assessment, such as, but not limited to green for benign, yellow for possibly malignant and red for probably malignant. Software classification thresholds are selected to minimize the difference between TP (true positives, fraction of malignant lesions correctly diagnosed) and TN (true negatives, fraction of benign lesions correctly diagnosed), choosing TN as close to TP as possible, with TN≦TP.

Image processing encompasses three stages. Stage 1 includes pre-processing, image segmentation, scoring, and best segmentation selection. Stage 2 includes image classification into benign or malignant lesions based on size difference and shape irregularity, as well as texture, color or other features. Stage 3 includes decision voting in terms of confidence based weighted averaging, bagging or boosting.

Figure 3:
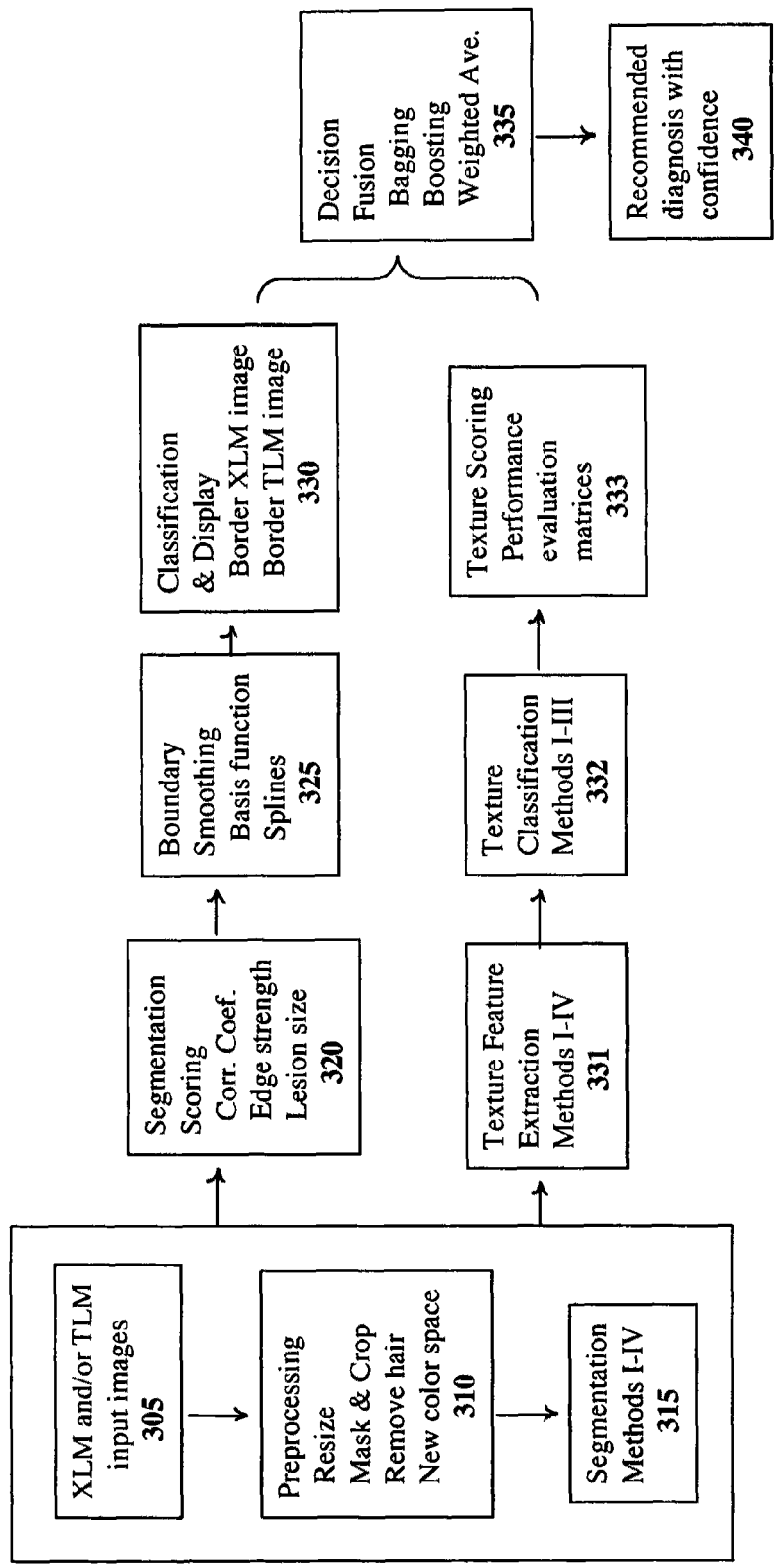
FIG. 3 is a flow chart that illustrates the automated steps of the software used in combination with the portable battery-powered handheld medical device

FIG. 3 depicts the automated imaging process 300 using the system/device and algorithms provided herein. One or more imaging modalities 305, e.g., XLM, TLM or other modalities, are used to capture a representation of the skin lesion. At step 310 Image Preprocessing occurs. This image is then digitized and made suitable for processing by a microprocessor. Several algorithms are then used to resize, filter, remove image artifacts, such as hair [1], optionally, change color space, such as, for example from RGB to HSI, to make images independent of a patient's skin color, and make background corrections. Calibration of the imaging device compensates for differences in imaging equipment.

At step 315 Image Segmentation extracts the lesion from the background and determines the lesion border. The methodology and difficulty of segmentation is correlated with the type and resolution of the imaging modality as well as the type of lesion. Thus, at this stage, several algorithms are use to segment a lesion, each following a different approach and emphasizing different lesion characteristics. Several known segmentation methods useful in the system include Sigmoid (TLM images), PCT (XLM images), PCT plus sigmoid, and Fuzzy c-Means. Also a novel segmentation method that is a region-fusion based segmentation with narrow band graph partitioning (NBGP), as described below, may be used. At step 320 the Scoring System chooses the best result among those produced by the various segmentation methods based on statistical properties of a lesion, such as correlation coefficient, edge strength, and lesion size [1-2], and heuristic approaches.

At step 325 post processing of the borders on the XLM and TLM images occurs. At step 330 Partial Classification uses objective measurements of lesion morphology, such as those based on ABCD (asymmetry, border, color, and diameter) rules, and other criteria, such as network, nodules, dots, and texture. Training sets and statistical correlations are used to develop mathematical models of feature combinations that indicate melanoma. These models typically use a weighted subset of lesion features. In this system, the normalized area difference between the TLM and XLM lesion images, and a heuristically set decision threshold, namely %Area Increase= (TLM area−XLM area)/TLM area [1], is used. A second independent partial classification is obtained from texture analysis of the lesion, including texture feature extraction 331, texture classification 332 and texture scoring 333. At step 335 Decision Voting uses confidence-based weighted averaging and/or bagging and/or boosting [2] to determine the final lesion classification that combines the partial classifications. At step 340, a recommended diagnosis can be made with confidence.

This classification system can implement several partial lesion classification schemes including three popular schemes currently accepted and trusted by dermatologists and the classification scheme described herein. Thus, the physician has the option to implement a partial lesion classification known and scrutinized in the art or the classification scheme described herein. Also, combining the results of the three known partial classification schemes, i.e., decision fusion, plus the instant classification scheme provides the second level of classification as described herein.

For example, in pre-processing hair artifacts are removed, or minimized, using median filtering with two structuring elements of size [1×5] and [5×1], after transforming the original RGB color image into a grayscale one using Y=0.3*R+ 0.59*G+0.11*B [24]. Background correction was accomplished using two methods. The first one assumes a multiplicative noise model for the non-uniform background. Initially a rough segmentation algorithm is used to remove the lesion from the image and then the image is transformed in polar coordinates. Since the ring artifact is brighter in the periphery and its intensity keeps decreasing towards the center of the lesion, then center of the lesion is found using a Hough transform. The missing values that represent the lesion are interpolated using a 5-7 degree polynomial and a goodness-of-fit test to automatically select the degree. The background is then computed as the median of intensity for all values of θ. Finally, the background-corrected image is computed by multiplying the original with the background (scaled between 0-1, to keep the range between 0-255).

The second method relies on homomorphic filtering, whereby an image is modeled as a product of illumination and reflectance components, i.e., f(x, y, ab)=i(x, y, a)r(x, y, b), where a, b are the color components (RGB). Initially a mask that contains regions with low intensity (intensity of the gray image less than $50^{th}$ percentile) and high frequency (high value of first derivatives) is prepared. Then for each rbg component $f_l(x,y)=\log(f(x,y,ab))$ is computed. the illumination component is modeled by a $4^{th}$ order polynomial surface, and to fit a surface to the data, the reflective newton method for minimization is used for each ab, after excluding regions corresponding to the previous mask. then, illumination is given by i(x, y, a)=exp(sp) and reflectance by r(x, y, b)=exp($f_r$−sp).

Also, for Image Segmentation there is provided a hierarchical region fusion framework algorithm, as shown in Algorithm 1, and a region-fusion based segmentation algorithm with narrow band graph partitioning (NBGP), as shown in Algorithm 2, which efficiently produces results very close to manual segmentation performed by specialists even for lesions that are highly asymmetric, have weak and/or false edges, strong hair, and bubble artifacts. The framework in Algorithm 1 is effective to automate the entire process. First, the image is segmented into small regions using active contours with strict constraints on homogeneity and strong edge. Then the small regions belonging to the same homogeneous cluster are merged together based on intensity centroid and gradient information. Evolution of Algorithms 1 and 2 is described in Example 2.

Algorithm 1

Obtained the preprocessed image $\Omega_0$
i = 0;
; Stage 1: Iterative Segmentation
while (1) do
    Apply Active Contours on $\Omega_i$;
    The output is the boundary $\Omega_{I+1}$ and its enclosed region $\Omega_{I+1}$;
    i = i + 1;
    if area($\Omega_{I+1}$)/area($\Omega_0$)<= MinArea or i == MaxNum then
        BREAK;
    end if
end while
; Stage 2: Region Merging
while (1) do
    if i == 1 then
        $\Omega_R = \Omega_1$;
        BREAK;
    end if
    if NOT(TESTMERGE($\Omega_1$; $\Omega_{I-1}$)) then
        $\Omega_R = \Omega_i$;
        BREAK;
    else
        MERGE($\Omega_1$; $\Omega_{I-1}$);
        i = i − 1;
    end if
end while
$\Omega_R$ is the segmented region;

Algorithm 2 summarizes the narrow band graph partitioning active contour for image segmentation.

Algorithm 2

Input: InitialCurve~C, MaxIterNum
iter $\Leftarrow$ 0
while iter $\Leftarrow$ MaxIterNum do
    ActivePixels=Reinitialize($\phi$);
    for every (x; y) 2 ActivePixels do
        Update(A(x; y));
    end for
    EXTRACTCURRENTCURVE( );
    if Converge then
        BREAK;
    end if
    iter = iter + 1;
end while
OUTPUTLATESTCURVE( );

The three steps in Algorithm 2 are described as follows:
Input: The input of the algorithm such as InitialCurve ~C, MaxIterNum, ebs, and ubs are provided by the user.

Step A is the ReInitialization Procedure. First, the level set function of each pixel is reinitialized locally [Reinitialize($\phi$)] to a signed distance function. To reduce the computational cost, a known approximation scheme was adopted [6]. Instead of using an exact sign distance function as the level set function Á, it is approximated within (ebs+ubs) layers of pixels. The zeroth layer is the current curve on which all level set function is zero. The four connected neighbors in both direction of the pixels on the curve, i.e., in the zeroth layer, constitute the first layer. The second layer consists the four connected neighbors of the first layer pixels that do not belong in the zeroth layer. The procedure continues until the (ebs+ubs)th layer is formed. All pixels of these (ebs+ubs)th layer are selected as ActivePixels. Then the layer number for all pixels inside the current curve will be multiplied by −1 to indicate that they are inside the region.

Step B is Curve Updating. Each pixel within the ActivePixels is then examined and its level set function is updated [Update($\phi$(i;j))] according to Eq. (15) in Example 2. An Upwind scheme is used for to calculate $|\nabla\phi|$. For a pixel (x; y), we need to know the feature of the point ((x, y)+b(~N)) in Eq. (21) must be known (Example 2). This feature, such as intensity, is approximated by the feature of the closest point to (x, y) on layer b. If more than one points are found, their average similarity measure will be used to update the function. Similar procedure is used for the term ((x, y)−b(N)) in Eq. (20). After the levelset function for all the ActivePixels are updated, the current curve is extracted within the narrow band by considering the zero level set crossings [ExtractCurrentCurve( )].

Step C is Convergence Control. If a certain number of iterations is reached (MaxIterNum) or the curve does not move [Converge] within two iterations, then the curve evolution is completed and the final curve is extracted [OutputLatestCurve]. Otherwise, Step B is repeated.

Also, Evolutionary Strategy (ES)-based segmentation to identify ROI on which to extract lesion features. The objective function we adopted favors an ellipse that divides the image into two homogeneous areas with minimum variation in both regions and it is given by $F(X,Y,a,b,\theta)=\int_\omega |I(x,y)-c_1|^2 dxdy + \int_{\Omega\setminus\omega} |I(x,y)-c_2|^2 dxdy$, where I(x,y) is the intensity value at coordinates (x, y), $\omega$ is the area enclosed by the ellipse defined by (X, Y, a, b, $\theta$), $\Omega$ is the area of the pixels whose intensity value is not zero, and $c_1$ and $c_2$ represent the average intensity value of the pixels inside and outside $\omega$, respectively. The results do not depend on initialization or threshold values and they are robust to artifacts and noise. Edge-based active contours also may be used such as geodesic active contours and gradient vector flow (GVF) snakes, which rely on gradient information.

Feature extraction uses lesion irregularity, color and texture. In considering lesion irregularity, lesion shape, one of the most important low-level image features to human perception, is highly irregular in cancerous lesions. Three measures for estimating lesion irregularity are total irregularity (IRtot):

$$IRtot = \frac{LesionArea}{LesionPerimeter^2},$$

sector irregularity (IRsec):

$$IRsec = \frac{1}{4}\sum_{i=1}^{4} \min_{j=1\ldots 4, j\neq i} |area(S_i) - area(S_j)|,$$

where Sj, I=1 . . . 4, are possibly overlapping sectors defined by four points on the lesion boundary that intersect with the minimum bounding rectangle and contour irregularity. Contour irregularity (IRcon) is given by $$IRcon = \sum_{j=0}^{n-1} |d_j - d_{j-1}|,$$

where $$d_j = \arctan\frac{y_j - y_{j-w}}{x_j - x_{j-w}} - \arctan\frac{y_{j-1} - y_{j-w-1}}{x_{j-1} - x_{j-w-1}}$$

represents the curvature at a boundary point $p_j=(x_j, y_j)$, when the boundary is given by a series of points $\{p_0\ p_1\ \ldots\ p_{n-1}\}$, with $p_0=p_n$.

For lesion texture analysis, gray-level co-occurrence matrices are very useful. For $N_d$ neighboring pixels separated by a distance d in direction θ, the Uniformity Energy (UE), Contrast (Cst), and Homogeneity (Hom) for d=1 and θ=0°, 45°, 90°, 135°, given by $$Hom = \sum_i \sum_j \frac{N_d[i,j]}{1+[i-j]}$$

and $$UE = \sum_i \sum_j N_d^2[i,j], \quad Cst = \sum_i \sum_j (i-j)^2 N_d^2[i,j],$$

is computed.

For lesion color, often the intensity of a lesion appears darker in malignant cases, and thus average intensity, extracted from gray-level images, is useful. Also, increased melanin in a malignant lesion will cause spots to occur. The bright/dark spot ratio is computed from top-hat and bottom-hat transforms. Additionally, irregularly distributed globules are predictive of melanoma, thus a globule dispersement index is computed, given by $$\bar{D} = \sum_{i=1}^{n} \frac{D_i}{n\sqrt{A}},$$

where $D_i$ is the distance of the i-th globule to the lesion centroid, n the globule count, and A the lesion area. Furthermore, we will include the percent melanoma color, color clustering ratio (CCR), and fuzzy ratio. CCR is the most powerful crisp feature to date, yielding approximately 87.5% overall diagnostic accuracy when applied to the inner 75% of the lesion.

As demonstrated in Example 5 the region-based active contours outperform thresholding and clustering based methods [3] and edge-based method (GVF). Using local features, the NBGP curve evolution scheme was able to produce the best segmentation results and achieved accuracy very close to manual segmentation results by specialists. It exhibited great robustness even for lesions with weak and/or false edges, highly asymmetric lesion, dense hair and bubble artifacts, and presence of noise.

Within the active contours, only the intensity feature of each pixel within the image is used. It is contemplated that an extension of algorithm would incorporate the color and texture features into the process, either independently, or combine them within the objective function, i.e., similarity measure. A generic framework that can incorporate different information forms (region and edge) of different nature (intensities, color, texture, and shapes) and can perform lesion segmentation efficiently for different imaging modalities is contemplated.

Thus, the portable, battery-operated, handheld system/device, including software and applicable algorithms, are useful in the early, real time detection of skin cancers, for example, but not limited to melanomas. The device is small enough to be easily placed into or retrieved from a pocket, such as a lab coat pocket. The device is therefore easily transported and utilized within the effective radius of the Bluetooth® module or other effective wireless technology. Because of the algorithms utilized to evaluate the image of the region of interest provide a rapid and accurate assessment, it is not necessary for an assessment to be performed by a specialist. A general practitioner is well able to perform an initial assessment with the device and to refer a patient to a specialist if the evaluation of the region of interest so warrants.

In a representative methodology a doctor, such as a general practitioner, visually identifies a skin lesion on a patients skin. Because the present device is easily carried on the doctor's person an assessment of the skin lesion can be performed immediately. The doctor may take a picture of the patient for archival purposes and add notes about the patient's demographics. The device is held above the skin lesion whereby the imaging component continuously captures and displays an image of the skin lesion which is viewed by the doctor on the display screen. The doctor aligns the image of the skin lesion and, optionally, selects an imaging modality, for example, XLM or TLM. The handheld device captures an image of the skin lesion.

The program running on the digital processor in the device analyzes the image of the skin lesion and makes a probability based determination on whether or not the lesion is benign or malignant using the algorithms described herein. The program provides its findings to the doctor in numerical and/or graphical form and displays the components of the image of the lesion that are indicators of malignancy. The general practitioner considers this information along with other factors and decides if the patient should see a specialized dermatologist.

The following examples are given for the purpose of illustrating various embodiments of the invention and are not meant to limit the present invention in any fashion.

EXAMPLE 1

Curve Evolution of Region-Based and Narrow Band Graph Partitioning Methods Level Set Formulation of Region-Based Curve Evolution Given an image $I \subset \Omega$, the region-based active contour model [4] finds the curve C that minimizes the energy based objective function:

$$E(\vec{C}) = \lambda_1 \int\int_{inside} |I(x,y) - c_1|^2 dx dy + \quad \text{Eq. (1)}$$
$$\lambda_2 \int\int_{outside} |I(x,y) - c_2|^2 dx dy + \mu L(\vec{C}) + \nu A(\text{inside } (\vec{C}))$$

where $c_1$ is the average intensity inside C; $c_2$ is the average intensity outside C; $\mu, \nu \geq 0$, and $\lambda_1, \lambda_2 > 0$, are fixed weight defined based on a priori knowledge. L(C) and A(C) are two regulation terms. Following Chan's practice [4], the weights are fixed as $\lambda 1 = \lambda 2 = 1, \mu = 1$, and $\nu = 0$ without the generality of the following derivation.

The main drawback of the explicit curve evolution (updating curve C directly) based on difference approximation scheme is that topological changes are di±cult to handle by such a evolving method. The levelset approach [5], however, handles such changes easily by defining the contour of a region as a zero-level set of a level set function ($\phi$) defined in the region $\Re$..

Thus, a plane curve C is represented as the zero level set of levelset function $\phi(x; y)$. The relation of a point $I(x; y)$ to the curve $\sim$C and levelset function $\phi(x; y)$ is given by:

$$\begin{cases} I(x,y) \text{ inside } \vec{C}, & \phi(x,y) > 0 \\ I(x,y) \text{ on } \vec{C}, & \phi(x,y) = 0 \\ I(x,y) \text{ outside } \vec{C}, & \phi(x,y) < 0 \end{cases} \quad \text{Eq. (2)}$$

Given this definition, the levelset formulation of Eq. (1) is:

$$E(\phi) = \int\int H(\phi(x,y))|I(x,y) - c_1|^2 dx dy + \quad \text{Eq. (3)}$$
$$\int\int (1 - H(\phi(x,y)))|I(x,y) - c_2|^2 dx dy +$$
$$\mu \int\int |\nabla H(\phi(x,y))| dx dy$$

where h(x) is the Heaviside step function.

Calculus of variation was used [4] to achieve local minimum of Eq. (3) by solving the following PDE, $$\frac{\partial \phi}{\partial t} = \delta_\varepsilon(\phi)\left(-(I-c_1)^2 + (I-c_2)^2 + \mu \, div\left(\frac{\nabla \phi}{|\nabla u|}\right)\right) \quad \text{Eq. (4)}$$

where $\delta_\varepsilon$ is the Dirac function, the derivative of the Heaviside step function in the $L^2$ space. Solving the equation Eq. (4) using implicit finite difference scheme gives the update of $c_1$ and $c_2$ in each iteration as shown in Eq. (5) and Eq. (6) respectively.

$$c_1 = \frac{\int\int H(\phi(x,y))I(x,y) dx dy}{\int\int H(\phi(x,y)) dx dy} \quad \text{Eq. (5)}$$

$$c_2 = \frac{\int\int (1 - H(\phi(x,y)))I(x,y) dx dy}{\int\int (1 - H(\phi(x,y))) dx dy} \quad \text{Eq. (6)}$$

Narrow Band Graph Partitioning Curve Evolution

The curve evolution method updates pixels close to the latest level set contour by optimizing the narrow band energy based similarity measure. A more generalized objective function than previously developed [6] is used to measure pairwise similarity between points p1 and p2:

$$\min_C E = \lambda_1 \int\int_{R_o}\int\int_{R_o} w_1(p_1,p_2) dp_1 dp_2 + \quad \text{Eq. (7)}$$
$$\lambda_2 \int\int_{R_i}\int\int_{R_i} w_2(p_1,p_2) dp_1 dp_2 +$$
$$\lambda_3 \int\int_{R_i}\int\int_{R_o} w_3(p_1,p_2) dp_1 dp_2 + \mu \oint_C ds$$

where the inward narrow band region Ri is bounded by curve C and C−biN, where ~N is the outward unit normal of curve C. Similarly, the outward narrow band region Ro is bounded by curve C and C+boN. Here, the bi and bo are fixed parameters that determine the size of the inward and outward narrow band. wk(k=1; 2; 3) are non-negative fixed weights for each region. In the first two terms, wk(k=1; 2) are dissimilarity measures for two points, p1 and p2, either both in the outward narrow band region (w1(p1, p2)), or both in the inward narrow band region(w2(p1, p2)). In the third term, w3 is a similarity measure two points, p1 and p2 each in the outward and inward narrow band(w3(p1, p2)). Different similarity measures can be used based on a priori domain knowledge.

Both regions, Ri and Ro, de−ned by the current curve C in the energy function Eq. 7 are most homogeneous within and have maximum difference between two regions. Unlike the cost function defined in [6], the sum of the −rst three terms depends on the curve and the parameters (wk) chosen and will not always be constant. Thus, none of them can be substituted with each other. Like the similarity measures, the weights can be chosen based on domain knowledge.

Variational Scheme for Narrow Band Region Energy

The curve evolution scheme for the minimization of the energy function in Eq. (7) based on gradient descent. Let M1 denotes the first term of Eq. (7), i.e., $M_1 = \lambda_1 \iint_{R_o}\iint_{R_o}\omega_1(p1, p2)dp_1 dp_2$. Following the gradient descent method [6], the derivative of $M_1$ with respect to time t can be derived as:

$$\frac{\partial M_1}{\partial t} = \oint_{\vec{C}_{ob}(t)} \langle \vec{C}_t, G_1, \vec{N}\rangle ds + \int\int_{R_o(\vec{C})} \frac{\partial}{\partial t} G_1(X,t) dX \quad \text{Eq. (8)}$$

where $C_{ob}(t)$ is the boundary curve of the region $R_o$ which is consisted of the curve C and the curve C+$b_o$N. The term $G_1(X, t)$ is defined as $G_1(X, t) = \iint R_0(C)\omega_1(X,Y) dY$. $G_2$ and $G_3$ are defined similarly for M2 and M3. The second term is positive within the narrow band defined by the curve C and C+$b_o$N and negative within the narrow band defined by C and C+$b_o$N. In addition, note that the similarity measures $\omega_k$ are not changing with respect to t.

The first term of Eq. (8) can be further decomposed as:

$$\oint_{\vec{C}_{ob(t)}} \langle \vec{C}_t, G_1, \vec{N}\rangle ds = \oint_{\vec{C}_o} \langle \vec{C}_{ot}, G_1\vec{N}\rangle ds - \oint_{\vec{C}} \langle \vec{C}, G_1\vec{N}\rangle ds \quad \text{Eq. (9)}$$

where $C_0$ is C+$b_o$N.

Based on the Frenet equation for a planar curve, we get $dN_i/ds = -\kappa T$, in which $N_i$ is the inward unit normal vector, and T is the unit tangent vector. Since the magnitude of both $N_i$ and T is unit $$\left|\frac{d(\vec{C}+b_o\vec{N})}{ds}\right|$$

which equals $T(1+b_o\kappa)=|1+b_o\kappa|$. Furthermore, $<b_oN_t, G_{1+}+N_t>=b_oG_{1+}<N_t,N_t>=b_oG_{1+}/2 \cdot N_t^2=b_oG_1/2 \cdot 1_t=0$ where $G_{1+}$ means the point X in $G_{1+}X$, t) is on the curve $C+b_oN$.

$$\oint_{\vec{C}_o}\langle \vec{C}_{ot}, G_1\vec{N}\rangle ds = \oint_{\vec{C}}\langle (\vec{C}+b_o\vec{N})_t, G_{1+}\vec{N}\rangle \left|\frac{d(\vec{C}+b_o\vec{N})}{ds}\right|ds \quad \text{Eq. (10)}$$

$$= \oint_{\vec{C}}\langle (\vec{C}+b_o\vec{N})_t, G_{1+}\vec{N}\rangle |1+\kappa b_o|ds$$

$$= \oint_{\vec{C}}\langle \vec{C}_t, |1+\kappa b_o|G_{1+}\vec{N}\rangle ds$$

Now, consider the second term in Eq. (8). Following the same procedure as above, but replacing $G_1(X, t)$ with $\omega_1(p_1, p_2)$, then $$\int\int_{R_o(\vec{C})}\frac{\partial}{\partial t}G_1(X,t)dX = \quad \text{Eq. (11)}$$

$$\int\int_{R_o(\vec{C})}\oint_{\vec{C}}\langle \vec{C}_t, (-w_1(p,\vec{C})+|1+\kappa b_o|w_1(p,\vec{C}+b_o\vec{N}))\vec{N}\rangle ds\,dp.$$

Substituting Eq. (10) and Eq. (11) into Eq. (8), then $$\frac{\partial M_1}{\partial t} = \quad \text{Eq. (12)}$$

$$2\oint_{\vec{C}}\left\langle \vec{C}_t, \left(\int\int_{R_o(\vec{C})}(-w_1(p,\vec{C})+|1+\kappa b_o|w_1(p,\vec{C}+b_o\vec{N})dp\right)\vec{N}\right\rangle ds$$

Following the same procedure, we can derive the derivatives of the second term (M2) and the third term (M3) in Eq. (7) with respect to t.

$$\frac{\partial M_2}{\partial t} = 2\oint_{\vec{C}}\left\langle \vec{C}_t, \left(\int\int_{R_i(\vec{C})}w_2(p,\vec{C})-|1-\kappa b_i|w_2(p,\vec{C}-b_i\vec{N})dp\right)\vec{N}\right\rangle ds \quad \text{Eq. (13)}$$

and $$\frac{\partial M_3}{\partial t} = \oint_{\vec{C}}\left\langle \vec{C}_t, \left(\int\int_{R_o(\vec{C})}w_3(p,\vec{C})-|1-\kappa b_i|w_3(p,\vec{C}-b_i\vec{N})dp + \int\int_{R_i(\vec{C})}|1+\kappa b_i|w_3(p,\vec{C}+b_o\vec{N})-w_3(p,\vec{C})dp\right)\vec{N}\right\rangle ds \quad \text{Eq. (14)}$$

Levelset Formulation of Narrow Band Graph Partitioning

Combining Eq. (8), (13), (14), and the curvature flow to minimize the regularization term, $\mu \oint_C ds$, in the energy function Eq. (7), the curve evolution scheme is obtained by letting the derivative of the energy E in Eq. (7) with respect to t to be 0. Using the level set formulation, the explicit curve evolution scheme is converted into explicit solution, assuming that $\phi(x, y)$ is a signed distance function for curve C in the Lipchitz space as defined in Eq. (2). Similar to levelset formulation of other region-based active contours, levelset evolution equation to minimize Eq. (7) is the following PDE, $$\frac{\partial \phi}{\partial t} = (A_i + A_o + \kappa)|\nabla \phi| \quad \text{Eq. (15)}$$

where $$A_i = \quad \text{Eq. (16)}$$

$$\int\int_{R_{i(x,y)}} -2\lambda_2|1-\kappa b_i|w_2(p,(x,y)-b_i\vec{N})+2\lambda_2 w_2(p,(x,y))-\lambda_3 w_3(p,(x,y))+\lambda_3|1+\kappa b_o|w_3(p,(x,y)+b_o\vec{N})dp$$

$$A_o = \quad \text{Eq. (17)}$$

$$\int\int_{R_{o(x,y)}} -\lambda_3|1-\kappa b_i|w_3(p,(x,y)-b_i\vec{N})+\lambda_3 w_3(p,(x,y))-2\lambda_1 w_1(p,(x,y))+2\lambda_1|1+\kappa b_o|w_1(p,(x,y)+b_o\vec{N})dp$$

The curve evolves based on the narrow band energy of $R_{o(x,y)}$ and $R_{i(x,y)}$ defined by $\kappa bi$ or $\kappa bo$. p denotes a pixel within the regions $R_{i(x,y)}$ or $R_{o(x,y)}$, each defined by the signed distance function $\phi(x; y)$:

$$R_{i(x,y)}=\{(\mu,\nu)|-b_i<=\phi(\mu,\nu)-\phi(x,y)<=0\} \quad \text{Eq. (19)}$$

$$R_{o(x,y)}=\{(\mu,\nu)|0<=\phi(\mu,\nu)-\phi(x,y)<=b_o\} \quad \text{Eq. (20)}$$

EXAMPLE 2

Skin Lesion Segmentation Algorithm Based on Region Fusion Narrow Band Graph Partitioning (NBGP)

Region Fusion Based Segmentation

At the first stage in Algorithm 1, active contours are applied iteratively inside each segmented regions. Based on the prior knowledge of the application, different strategies can be chosen to further segment only regions with lower intensity, higher intensity, or both. In the skin lesion segmentation, since the skin lesion always have lower intensity than that of the skin and blood volume, regions are always segmented with lower intensity further. The iterative segmentation procedure stops when the number of pixels inside the region is smaller than MinArea % of the total number of pixels in the image. For the skin lesion segmentation, based on extensive test, MinArea=10 was chosen. This makes sure that small lesions can be correctly segmented, while avoiding an over segmentation problem.

Figures 4A, 4B, 4C, 4D:
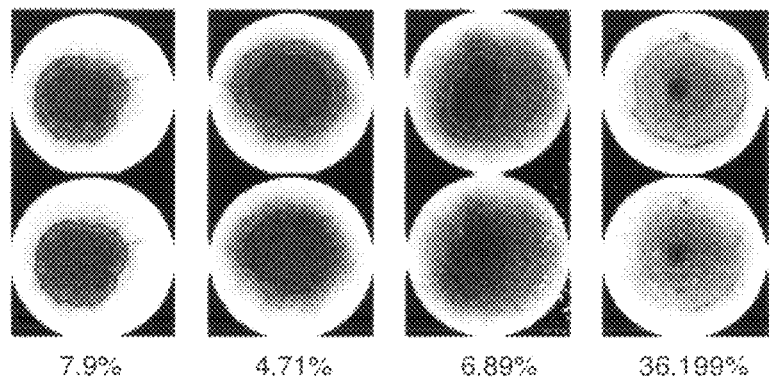
FIGS. 4A-4D depict results of TLM image segmentation. The top image show the results of the hierarchical region fusion algorithm using Chan-Vese active contour. Red, blue, and green boundary represent the result of the first three iterations. The bottom images show the final results. Error ratios for each pair of images are shown.
Figures 5A, 5B, 5C, 5D:
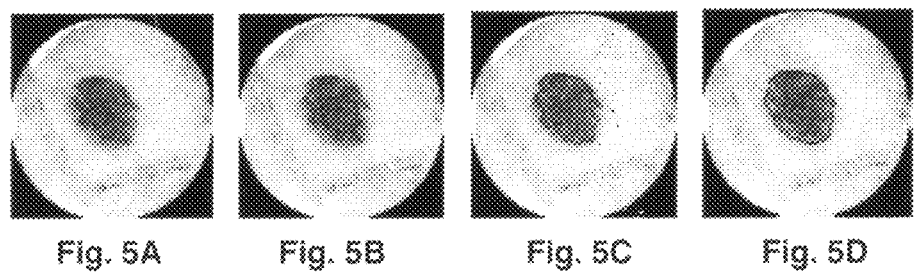
FIGS. 5A-5H show results of the segmentation of two XLM images. The XLM images show initial curves (FIGS. 5A, 5E), curves after 10 iterations (FIGS. 5B, 5F), results of Chan-Vese' method (FIG. 5C, 5G), and results of NBGP method (FIG. 5D, 5H).
Figures 5E, 5F, 5G, 5H:
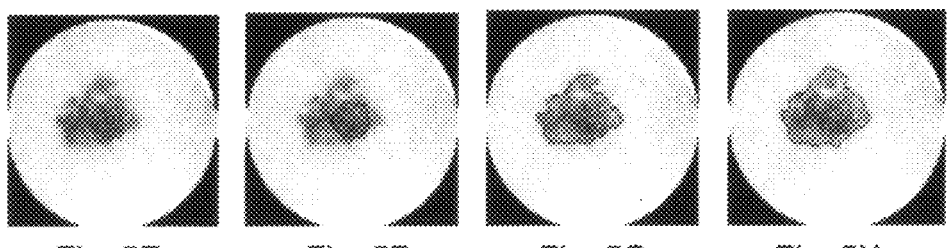

The second stage merges overlapping and/or non-overlapping regions based on two criteria [Testmerge( )]. The centroid criterion looks at the absolute difference of the intensity centroid, $$\theta \subseteq \mathfrak{R}.$$

of adjacent small regions and merge the regions together if it falls below a threshold τ. The edge strength is defined as the average gradient magnitude of pixels inside the dilated boundary, the same as used in the scoring system [3]. If the edge strength of the inside region Si is greater than that of the outside region So, i.e., Si>So, then the two regions are merged together. The area with higher edge strength is preferred based on this gradient criterion. FIGS. 4A-4D show that the two criteria work successfully when the blood in large vessels is not presented (FIGS. 4A-4B) and when it is presented (FIGS. 4C-4D). The blood in large vessels are included in the red boundary when we apply Chan-Vese model one time.

Narrow Band Graph Partitioning Image Segmentation Algorithm

Only a rough estimation is required to direct the curve evolution. The estimation procedure can make the algorithm faster by reducing the amount the time required to solve the PDE. In Algorithm 2, the curve evolution is further speeded up by evolving over a relatively small ring (Narrow Band) for both levelset function update and region-based energy similarity measure. The narrow band size for levelset function update is denoted as ubs. Pixels inside this band belongs to ActivePixels. For the region-based similarity measure, we assume the inward and outward narrow band has the same size, denoted as ebs. In Algorithm 2, the simplified levelset solution (from Eq. (16) and Eq (17)) is used for curve evolution Eq. (15) as detailed below. Assuming the narrow band size is small and the curve is sufficiently smooth, then $b_i\cdot$ and $b_o\cdot$ will approach zero. Thus, the equations for Ai and Ao can be simplified as:

$$A_i = \iint_{R_{i(x,y)}} -2\lambda_2 w_2(p, (x, y) - b_i \vec{N}) + 2\lambda_2 w_2(p, (x, y)) - \quad \text{Eq. (20)}$$
$$\lambda_3 w_3(p, (x, y)) + \lambda_3 w_3(p, (x, y) + b_o \vec{N}) dp$$

$$A_o = \iint_{R_{o(x,y)}} -\lambda_3 w_3(p, (x, y) - b_i \vec{N}) + \lambda_3 w_3(p, (x, y)) - \quad \text{Eq. (21)}$$
$$2\lambda_1 w_1(p, (x, y)) + 2\lambda_1 w_1(p, (x, y) + b_o \vec{N}) dp$$

Essentially, this is equal to treat the arc-length element $|(dC+b_o N)/ds|$ and $|(dC-b_i N)/ds|$ as constants whose values are 1.

Computational and Space Complexity Analysis

Several techniques are employed to reduce the computational cost. First of all, the fast implementation of active contours [7] is used for all curve evolution. As detailed in Example 1, instead of solving the objective function defined in Eq. (1) directly at each iteration, the sign of a levelset function φ(x; y) on a pixel p(x; y) is used to indicate the changes. This is sufficient for segmentation purpose. When the objective function decreases, the sign of the φ(x; y) on p(x; y) changes; otherwise, it will remain the same as in the last iteration. The discrete form of the spatial constraint, i.e., the length term in Eq. (3), is shown in Eq. (22) which is the same as previously described [7].

$$\nabla H(\phi(x,y)) = ((H(\phi(x+1,y)) - H(\phi(x,y))), (H(\phi(x,y+1)) - H(\phi(x,y)))) \quad \text{(Eq. 22)}$$

The time complexity of the level set based curve evolution is proven [7] to be O(M×N) where M×N is the total number of pixels of the image.

Secondly, while updating the levelset function, a previously proposed [8] and extensively analyzed and optimized [9] narrow band approach was used. The idea is to consider only the pixels close to the current contour, i.e., ActivePixels. To reduce the cost of updating the narrow band itself from iteration to iteration, the contour position and the set of narrow band pixels are updated only in cases where the contour is very close to the borders of the current band. A significant cost reduction can be achieved through this approach [10].

In order to further reduce the computational cost, a multi-scale technique is used and combined with the narrow band graph partitioning curve evolution algorithm. Specifically, a Gaussian pyramid of images is built upon the full resolution image and similar narrow band active contour problems are defined across the different granularity levels. Usually this technique is applied to a pyramid with two or three levels.

Considering all these mechanisms, the computational complexity of segmentation Algorithm 2 is analyzed here. For an image with dimension N×N, the number of ActivePixels is 2×ubs×N. For each pixel in ActivePixels, the total number of pixels in outward and inward narrow band region is 2×ebs×N. Thus, the computational complexity of the FOR loop in Algorithm 2 to update the level set function φ is $O(4\times ebs\times ubs\times N^2)$. For small ebs and ubs, such that ebs/N<0:1 and ubs≦2, the computational complexity is $O(N^2)$. For the re-initialization function, Reinitialize(φ), in Algorithm 2, the layer number is assigned to pixels based on four-connected neighbors. The number of pixels inside the (ebs+ubs) layer is 2×(ebs+ubs)×N. For small (ebs+ubs), the computational complexity of function Reinitialize(φ) is O(N).

The overall computational complexity of skin lesion segmentation algorithm is $O(N^2)$ when the image size is N×N, linearly related to the MaxIterNum×LevelNum, in which MaxIterNum is the maximum iteration number of the curve evolution NBGP algorithm, and the LevelNum is the number of multiple scale used in the Gaussian pyramid. This is much better than the computational complexity of $O(N^2)$ for image segmentation based on graph partitioning active contour [6]. For skin lesion image segmentation, when using a 64 bit AMD machine with 2.4 GHz Opteron processors and 2 GB RAM, the runtime of our MATLABrprogram ranges from 104 seconds (for image size 577×397) to 923 seconds (for image size 2465×1637).

EXAMPLE 3

Application of Segmentation Algorithm

Image Acquisition

XLM and TLM images were acquired with two Nevoscope [34,35] that uses a 5× optical lens (manufactured by Nikon, Japan). An Olympus C2500 digital camera was attached to this Nevoscope. Fifty one XLM images and sixty TLM images were used. The image resolution is 1712×1368 pixels. Region of interests (ROI) was identified in every image and segmentation, manually by dermatologists and automatically using our method, was performed on a 236×236 region obtained from a preprocessing step described in the next section. Results from manual segmentation were used as reference in evaluations. In addition, one hundred ELM images were acquired using oil immersion technique [11-12]. Among them, thirty images were melanoma and the rest were benign. Three dermatologists performed segmentation on the original image scale. The average contour was used as reference in our experiments.

Pre-Processing and Parameter Settings

To improve the computational cost without sacrificing the segmentation results, TLM and XLM images were resized to a 256×256. In image acquisition, careful measurement was taken such that lesion appears close to the center of the images. To find appropriate ROI, Canny edge detector was applied to extract boundaries of the peripheral dark area. The center of a rectangular ROI was identified by Hough transform. The size of ROI is bounded by circular boundary extracted earlier and hence at 236×236. A median filter and a Gaussian filter were applied to smooth the image and reduce the noise. The filter size is 5×5 and the standard deviation for the Gaussian filter is 1:5.

Table 1 summarizes the experimental parameters. The initialization in active contours was randomly generated close to the center of an image in a 10×10 square for XLM images and in 40×40 square for the TLM images. The rational for parameter selection for XLM and TLM images is to encourage homogeneity of outward narrow band than the inward narrow band since skin lesions usually vary in intensity distribution while healthy skin appears more uniform.

TABLE 1

| Image | MA | TS | IT | µ | ebs | ubs | λ1 | λ2 | λ3 |
|---|---|---|---|---|---|---|---|---|---|
| XLM | No | 0:1 | 10 | 255 | 10 | 1 | 1:5 | 0:5 | 0:5 |
| TLM | No | 0:1 | 10 | 255 | 10 | 1 | 1:5 | 0:5 | 0:5 |
| ELM | Yes | 0:1 | 10 | 255 | 10 | coarse scale: 2 | 5 | 0 | 1 |
|  |  |  |  |  |  | fine scale: 1 | 1 | 0:5 | 1 |

MA: Multi-scale Approach; TS: Time Step; IT: Maximum Number of Iteration

The size of ELM images varies from 577×397 to 2465×1637. Hence, the original image was used without resizing. To compensate for size-induced computational cost, a multi-scale Gaussian pyramid is employed. The boundary obtained through Algorithm 2 on the coarse scale is used as the initial curve on the finer level. Three decomposition scale was used and the third level refers to the original image. The rational of parameter selection for coarse scales (the first and second scales) is to ensure homogeneity in the outward band of the boundary while allow the inward band to include inhomogeneous structures. At the third scale, parameters were chosen to avoid misleading boundary evolution due to noisy pixels and structures (very small region of irregularity) on the background healthy skin. For the curve evolution, the similarity measure used [6]:

$$\omega 1(p1;p2) = \omega 2(p1;p2) = -\omega 3(p1;p2) = |I(p1) - I(p2)|;$$

where I(p) is the intensity of pixel p.

Performance Analysis

The quantitative metrics used in [3] were adopted for the performance evaluation. An error rate E is defined as the normalized agreement of segmentation results and the reference. Let c denote the contour of the segmentation result and or is the reference contour. Function A(c) gives the area enclosed by contour c. The error rate is formulated as follows:

$$E = \frac{A(c) \oplus A(c_r)}{A(c) + A(c_r)} \quad \text{(eq. 23)}$$

A similarity metric was used [38] as follows:

$$S = \frac{2 \times A(c) \cap A(c_r)}{A(c) + A(c_r)} \quad \text{(eq. 24)}$$

It is obvious that E+S=1.

FIGS. 5A-5H illustrate segmentation results of two XLM images. This method demonstrated significant improvements in error rate. In FIGS. 5A-5D, the error rates for this method and Chan-Vese's method are 4:3% and 12:26%, respectively. In FIGS. 5E-5H the error rates for NBGP and Chan-Vese's methods are 5:34% and 10:69%, respectively. FIGS. 6A-6F illustrate segmentation of two TLM images. In FIGS. 6A-6C, both methods segmented the large lesion successfully with low error rate. NBGP and Chan-Vese's (CV) method achieved error rates at 5:47% and 5:18%, respectively. In FIGS. 6D-6F NBGP demonstrated improved accuracy over a small lesion with an error rate of 23:36%; whereas the error rate of Chan-Veses's method was 30:52%.

A comparison study was performed with known methods [3-4] and the average error rate (%) and standard deviation is summarized in Table 2. The experimental images consist of 51 XLM images and 60 TLM images. In both image modalities, NBGP exhibits significantly improved performance. The average error ratios were 12:41% and 12:28% for XLM and TLM images, respectively. Those were more than 30% improvement in error rate. Box plots are shown in FIGS. 7A-7B. The NBGP method demonstrated small variance in experiments and resulted in the best results in the average error ratio, and the first quarter, the median, and the third quarter of the distribution. Although the lowest error ratio in both cases were achieved by other methods, the NBGP method was consistent and significant accurate on average.

TABLE 2

| Error | NBGP | CV | SS | PCT | SPCT | FC |
|---|---|---|---|---|---|---|
| XLM | 12.41 | 13.7 | 15.15 | 18.88 | 16.57 | 15.22 |
| STD | (±10:2%) | (±8:5%) | (±15:2%) | (±12:6%) | (±14:8%) | (±15:4%) |
| TLM | 12.28 | 12.67 | 14.08 | 23.09 | 19.22 | 16.57 |
| STD | (±8:5%) | (±9:0%) | (±13:9%) | (±22:1%) | (±18:0%) | (±18:3%) |

SS: Scoring System; PCT: Principal Component Transform method; SPCT: Sigmoid-based PCT method; FC: Fuzzy C-Mean The improved performance of NBGP is two fold. First, The µ×L term in Eq. (1) places a spatial constraint for the curve evolution. Studies have shown that Chan-Vese method can be implemented by nonlinear diffusion preprocessing followed by K-mean clustering [39]. Second, the hierarchical region-fusion approach emphasizes homogeneity outside the object contour more than inside of it and hence is less affected by blood volume in large vessels, even when the lesion is very small. FIGS. 8A-8C illustrate segmentation failure resulting from other methods [3]. This is due to the presence of blood in large vessels that causes smooth transition of color. In comparison, result from our method is shown in FIG. 6F.

For the ELM images, three dermatologists performed lesion segmentation manually to create the reference set. The NGBP segmentation method was compared with Chan-Vese's method and the variation among manual segmentation results also was studied. In many cases, Chan-Vese's method achieved good results. An example is shown in FIGS. 9A-9B. For images with asymmetric lesions, however, Chan-Vese's method faced difficulties at finding all lesion area. FIGS. 10A-10H illustrate examples of segmenting asymmetric lesions. FIGS. 10A-10D show segmentation contour superimposed on the input images by Chan-Vese's method. Because the imbalanced lesion intensity, the algorithm failed to findnd the complete region. The failure occurred mostly in the higher intensity part where lesion is not well-defined. FIGS. 10E-10H show results from the NGBP method. The skin lesions were successfully delineated in the presence of asymmetric property and hair distortion.

Figure 11A:
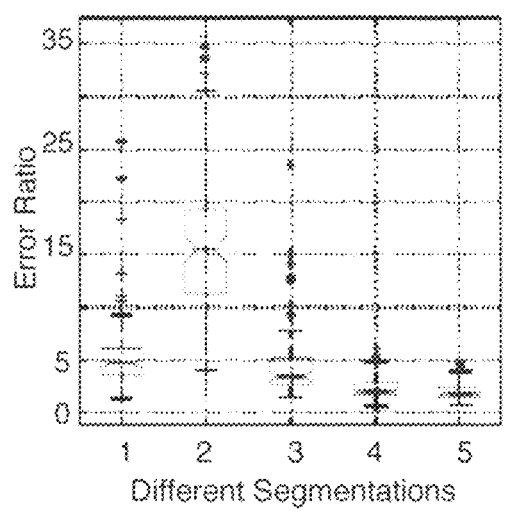
FIGS. 11A-11B depict the segmentation error ratio (FIG. 11A) and the error ratio between NBGP and manual results (FIG. 11B).

The average error ratio of the ELM images from two active contour-based segmentation methods and manual segmentation with standard deviation is 5.44±3.6% for NBGP, 16.52±7.1% for Chan-Vese and 4.45±3.2%, 2.28±11.1% and 2.01±0.8% for the three dermatologists. The reference is the average of manual segmentation results. FIG. 11A shows the distribution of the error ratio for the 100 ELM images.

Figure 11B:
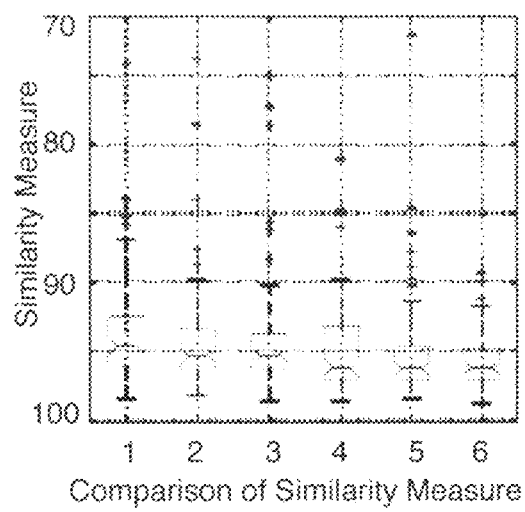

Area similarity measure, Eq. (24), also is used to compare the variability among dermatologists and the NBGP algorithm (FIG. 11B). The average similarity measures for ELM images are shown in Table 3. The error ratio of the comparison in FIG. 11B and similarity measures in Table 3 show that the performance of the NBGP algorithm are very close to the performance of domain experts and both performance are consistent with respect to the ground truth.

TABLE 3

|  | Area Similarity | STD |
| --- | --- | --- |
| NBGP-Dr. G | 93.93% | ±3:4% |
| NBGP-Dr. S | 94.27% | ±3:6% |
| NBGP-Dr. M | 94:27% | ±3:8% |
| Dr. G-Dr. S | 95:85% | ±3:3% |
| Dr. G-Dr. M | 95:27% | ±3:4% |
| Dr. S-Dr. M | 95:75% | ±1:9% |

EXAMPLE 6

Accuracy of Partial Labeling

Twenty three lesions of known histopathology were classified as shown in Table 4, which shows a sensitivity of 80%, specificity of 92.3%, and an overall accuracy of 86.9%. Thus, measuring increased vascularization as the area difference between the XLM and TLM images is an excellent criterion for malignancy detection, as it approaches closely the performance of dermatologists (80% and 60%) and dermoscopy experts (90% and 59%), respectively. Table 4 shows the difference between a malignant and a benign lesion when the TLM (left column) and XLM (right column) images are processed. The lesions in the upper row represent a mild dysplastic nevus (benign), while the images in the lower row correspond to a compound nevus (malignant). The malignant lesion has a much larger area in the TLM image that corresponds to blood vessels developed to support the growing cancer, while the benign lesion has the same area in both images.

Figure 12A:
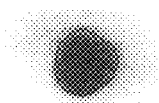
FIGS. 12A-12D depict TLM (FIGS. 12A-12B) and XLM (FIGS. 12C-12D) images of benign (FIGS. 12A, 12C) and malignant (FIGS. 12B, 12D) lesions.
Figure 12B:
Figure 12C:
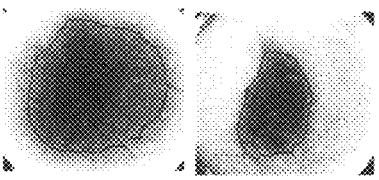
Figure 12D:
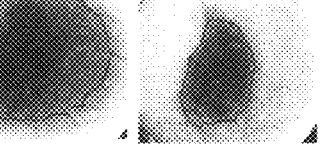
Figure 13A:
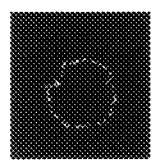
FIGS. 13A-13E illustrate original boundary (FIG. 13A), basis function boundary (FIG. 13B), minor ridges (FIG. 13C), smooth boundary (FIG. 13D), and smooth boundary on original image (FIG. 13E).
Figure 13B:
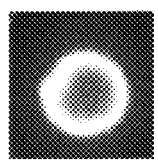
Figure 13C:
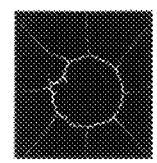
Figure 13D:
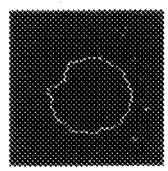
Figure 13E:
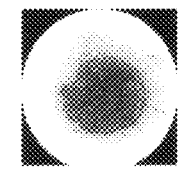

Thirty three lesions with known histopathology results were classified as shown in the confusion matrix reported in Table 5, which shows a sensitivity of 100%, specificity of 78.3%, and an overall accuracy of 84.8% in determining the malignancy of a lesion (FIGS. 12A-12B).

TABLE 4

Classification Results
Vascularization Measurement

|  |  | Predicted | |
| --- | --- | --- | --- |
|  |  | Malignant | Benign |
| Actual | Malignant | 12 | 1 |
|  | Benign | 2 | 8 |

TABLE 5

Classification Results
Texture Analysis

|  |  | Predicted | |
| --- | --- | --- | --- |
|  |  | Malignant | Benign |
| Actual | Malignant | 10 | 0 |
|  | Benign | 5 | 18 |

EXAMPLE 7

Smooth Boundary Computation

Regardless of the method used, at the end of segmentation a binary image (mask) that corresponds to the lesion is defined. then, the area and boundary of the lesion can be computed as follows: 1) perform the morphological operations of dilation, erosion, and bridging on the binary image to fill in the holes within the lesion and make it homogeneous, 2) compute the lesion boundary as the set of all nonzero pixels that are connected to at least one zero-valued pixel in the binary image. remove the spurs from the lesion boundary and skeletonize the image to get a boundary that is only one pixel thick and 3) compute the area of the segmented lesion as the number of pixels that lie within the lesion boundary.

For boundary smoothing a parametric curve model is used to obtain a smooth continuous contour from the disjoint edges of the boundary. the curve is identified as follows. First, for each pixel in the image the sum of the square root of distances from each boundary pixel is calculated, and this value is assigned to the corresponding pixel in a new 2-D image array, which defines a "basis function." Then, a new 2-d binary array representing the "minor ridges" is formed from the basis function from the gradients of the pixels. Second, morphological operations are performed to remove the extra spurs and to clean the isolated pixels, and the resulting image is skeletonized to obtain a smooth image boundary. Third, optionally, these points can be fitted with a spline to get an even smoother boundary. Finally, the curve is superimposed on the original image to visualize the smooth lesion boundary. FIGS. 13A-13E show the various steps needed to obtain a smooth lesion boundary.

The following references are cited herein.
1. Yuan et al. IEEE EMBS Annual International Conference, New York City, N.Y., Aug. 30-Sep. 3, 2006.
2. Situ et al. Automatic Segmentation of Skin Lesion Images using Evolutionary Strategy, ICIP 2007, San Antonio, Tex., Sep. 15-19, 2007

3. Zouridakis et al. Proceedings of the 26<sup>th</sup> Annual International Conference of the IEEE, EMBS, IEEE, pp. 1596-1593, 2004.
4. Chan, T. F. and Vese, L. A. IEEE Trans. Image Processing 10(29):266-277, 2001.
5. Osher, J. S. Journal of Computational Physics, 79:12-49, 1988.
6. Sumengen, B. and Manjunath, B. S. IEEE Trans. Pattern Anal. Mach. Intell, 28)4):509-521, 2006.
7. Song, B. and Chan, C. Fast algorithm for level set based optimization, 2002.
8. Chop, D. J. computational physics, 106(1):77-91, 1993.
9. Adalsteinsso, D. and Sethian, J. Computational Physics, 3(118):269-277, 1995.
10. Paragios, N. and Deriche, R. IEEE Trans. Pattern Anal. Mach. 22(3):266-280, 2000.
11. Celebi et al. International Conference on Information Technology: coding and Computing, ITCC 2005, Proceedings, IEEE, pp. 163-168, 2005.
12. Celebi et al. International Conference on Information Technology: coding and Computing, ITCC 2005, Proceedings, IEEE, pp. 123-128, 2005.

Any patents or publications mentioned in this specification are indicative of the levels of those skilled in the art to which the invention pertains. These patents and publications are incorporated by reference herein to the same extent as if each individual publication was incorporated by reference specifically and individually. One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A device for screening the skin of an individual in real time, comprising:
   in a self-contained, hand-held and portable means for housing the device:
      means for programming the device;
      means for controlling interaction with a user of the device;
      means for acquiring and displaying an image of a region of interest on the skin of an individual;
      means for analyzing and classifying the image comprising a region-fusion based segmentation with narrow band graph partitioning algorithm with an active contour model; and
      means for controlling one or both of an exchange of data with a personal computer or a receipt of software from a personal computer.

2. The device of claim 1, further comprising means for powering the device.

3. The device of claim 2, wherein the means for powering the device comprises a power management unit having a battery, a battery charger, a supervisor and voltage regulators.

4. The device of claim 1, wherein the means for programming the device comprises: a programmable digital signal microprocessor with a memory storing processor executable instructions; and a boot flash for parallel flash memory.

5. The device of claim 1, wherein the means for controlling interaction with a user of the device comprises: a human machine interface board, including a keypad and one or more display terminals; and a user interface.

6. The device of claim 5, wherein the display terminals comprise one or both of an on-board display terminal or an off-board display terminal.

7. The device of claim 1, wherein the means for acquiring and displaying the image of the skin comprises: a sensor having a combination of one or more light sources and one or more imaging sensors for image acquisition; a video encoder to convert the acquired digital image as an analog off board image; and an on board visual display.

8. The device of claim 1, wherein the means for controlling one or both of an exchange of data with a personal computer or receipt of software from a personal computer comprises a device configured to wirelessly communicate between a programmable digital signal microprocessor comprising the handheld screening device and a personal computer, including a parallel for a Universal Asynchronous Receiver/Transmitter.

9. A device for screening a region of interest on the skin of an individual in real time, comprising:
   in a self-contained, hand-held, portable housing, a programmable digital signal microprocessor with a memory storing processor executable instructions digitally linked to:
      a boot flash for parallel flash memory digitally connected to the microprocessor;
      an input device;
      a sensor having a combination of one or more light sources and one or more imaging sensors;
      a digital to analog signal video encoder connected to an off-board display terminal;
      an on-board display terminal;
      a wireless device configured to wirelessly communicate between the programmable digital signal microprocessor and a personal computer, including a parallel for a Universal Asynchronous Receiver/Transmitter;
      a power management unit;
      a module for pre-processing and image segmentation of the region of interest comprising region-fusion based segmentation with narrow band graph partitioning algorithm with an active contour model;
      a module for image classification of a lesion found within the region of interest as a benign or malignant lesion as determined by one or more of a size difference, shape irregularity or texture formation each of which comprises a partial classification;
      a module for decision voting in terms of confidence based weighted averaging of the partial classifications; and
      a module for image reconstruction for three-dimensional imaging of the region of interest.

10. The device of claim 9, wherein the input device is a keypad or a touch screen.

11. The device of claim 9, wherein the light source(s) emit visible or invisible light arranged in different spatial configurations and wherein the imaging sensor(s) is an optical camera, an infrared camera, a thermal camera, a three dimensional stereo camera or a digital light processing sensor.

12. The device of claim 9, wherein the power management unit comprises a battery, battery charger, supervisor, and two voltage regulators.

13. A method for screening the skin of an individual in real time, comprising:
   acquiring one or more images of a region of interest on the skin in one or more modalities with the device of claim 1;
   displaying the acquired image;
   preprocessing the acquired image(s) using the region-fusion based segmentation with narrow band graph partitioning algorithm with an active contour model;

classifying the region of interest on the skin as benign or malignant; and displaying the classification results.

14. The method of claim 13, further comprising: wirelessly communicating the classification results to a personal computer.

15. The method of claim 13, wherein the imaging modality is XLM or TLM.

16. The method of claim 13, wherein preprocessing comprises extracting a lesion from the background of the image and determining a lesion border.

17. The method of claim 13, wherein classifying the lesion comprises confidence based weighted averaging of a combination of partial classifications based on one or more features of the lesion.

18. The method of claim 17, wherein the features of the skin lesion include a size difference, shape irregularity or texture formation.

19. The method of claim 13, wherein displaying the classification comprises color coding the results.

20. A digital processor-implemented system for classifying a region of interest on the skin of an individual, comprising:
  a module for pre-processing and image segmentation of the region of interest comprising a region-fusion based segmentation with narrow band graph partitioning algorithm with an active contour model;
  a module for image classification of a lesion found within the region of interest as a benign or malignant lesion as determined by one or more of a size difference, shape irregularity or texture formation each of which comprises a partial classification;
  a module for decision voting in terms of confidence based weighted averaging of the partial classifications; and
  a module for image reconstruction for three-dimensional imaging of the region of interest.

21. The processor implemented system of claim 20, further comprising a module for wireless communication between the processor and a personal computer.

22. A processor readable medium having processor-executable instructions to perform a method for detecting skin cancers on an individual in real time, said method comprising the steps of:
  acquiring one or more images of a region of interest on the skin in one or more modalities;
  preprocessing the acquired image(s) comprising extracting a lesion from the background of the image and determining a lesion border using a region-fusion based segmentation with narrow band graph partitioning algorithm with an active contour model;
  classifying the skin lesion as benign or malignant by a confidence based weighted averaging of a combination of partial classifications based on one or more features of the lesion; and
  displaying the classification results.

23. The processor readable medium of claim 22, wherein the imaging modalities are XLM or TLM.

24. The processor readable medium of claim 22, wherein the features of the lesion include a size difference, shape irregularity or texture formation.

25. The processor readable medium of claim 22, wherein displaying the classification comprises color coding the results.

* * * * *